United States Patent [19]

Buschek et al.

[11] Patent Number: 4,476,223
[45] Date of Patent: Oct. 9, 1984

[54] PROCESS FOR THE STABILIZATION OF AQUEOUS SOLUTIONS OF CHOLESTEROL ESTERASE FROM PSEUDOMONAS

[75] Inventors: Herbert Buschek, Weilheim; Helmut Schlumberger, Polling; Joachim Siedel, Bernried, all of Fed. Rep. of Germany

[73] Assignee: Boehringer Mannheim GmbH, Mannheim-Waldhof, Fed. Rep. of Germany

[21] Appl. No.: 452,690

[22] Filed: Dec. 23, 1982

[30] Foreign Application Priority Data

Jan. 7, 1982 [DE] Fed. Rep. of Germany ....... 3200274

[51] Int. Cl.³ .......................... C12N 9/96; C12N 9/18; C12Q 1/60

[52] U.S. Cl. ...................................... 435/188; 435/11; 435/197

[58] Field of Search .......................... 435/188, 11, 197

[56] References Cited

U.S. PATENT DOCUMENTS

| | | | |
|---|---|---|---|
| 4,343,903 | 8/1982 | Beaucamp et al. | 435/197 |
| 4,360,596 | 11/1982 | Beaucamp et al. | 435/197 |
| 4,409,326 | 10/1983 | Modrovich | 435/11 |

*Primary Examiner*—Lionel M. Shapiro
*Attorney, Agent, or Firm*—Felfe & Lynch

[57] ABSTRACT

The present invention provides a process for the stabilization of an aqueous solution of cholesterol esterase from Pseudomonas, especially in the presence of a surface-active agent, wherein the enzyme is dissolved in a phosphate-free buffer which contains 10 to 200 mMol/liter of magnesium ions.

10 Claims, 3 Drawing Figures

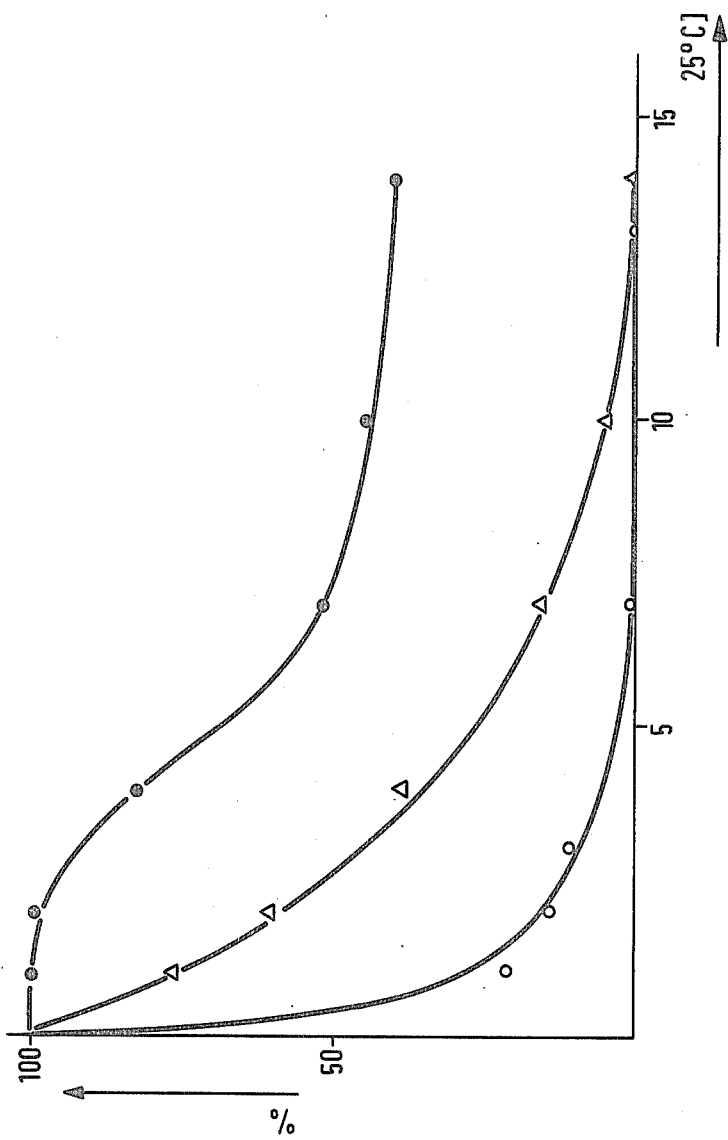

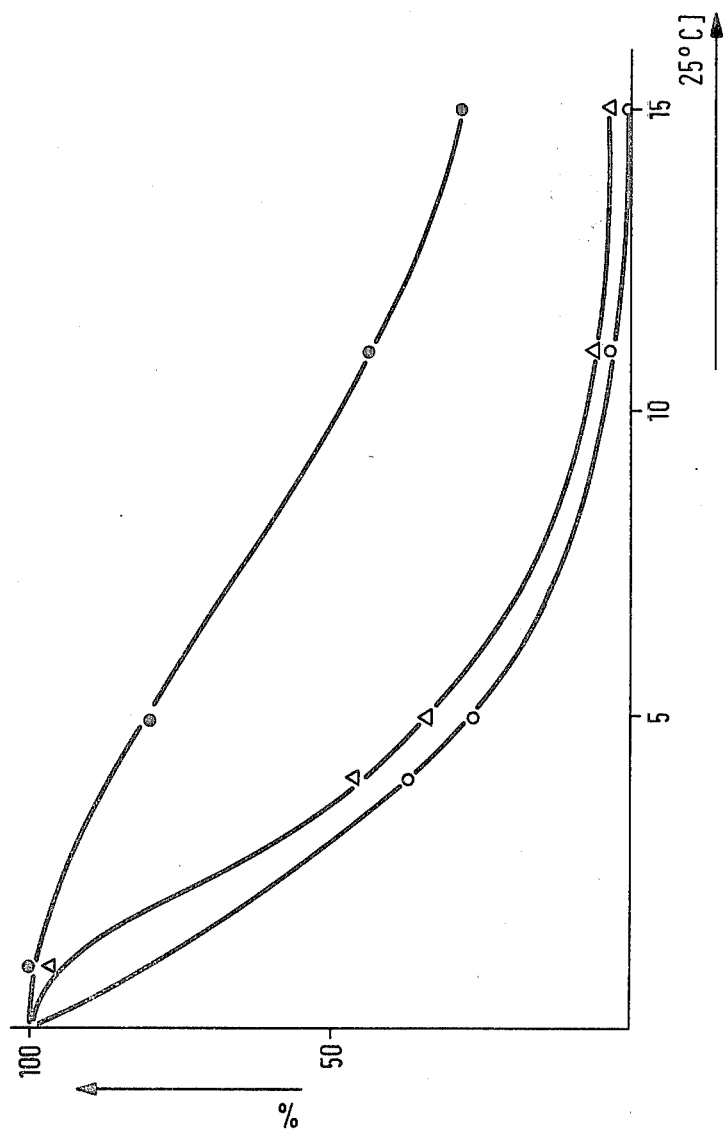

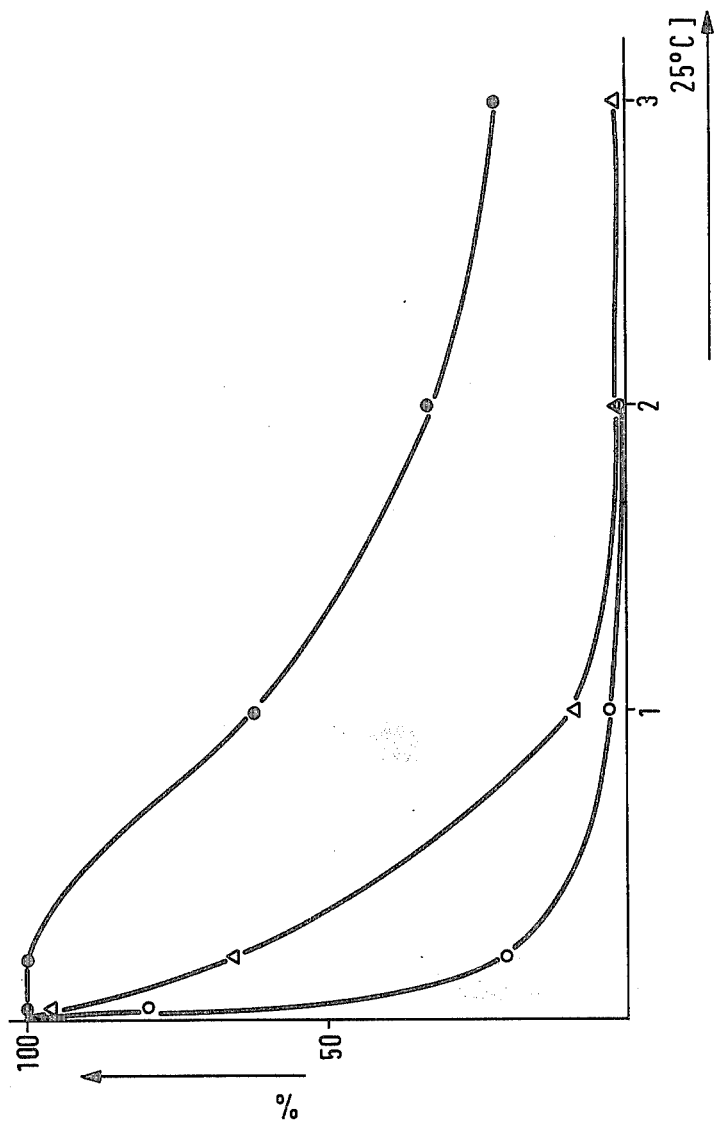

PROCESS FOR THE STABILIZATION OF AQUEOUS SOLUTIONS OF CHOLESTEROL ESTERASE FROM PSEUDOMONAS

The present invention is concerned with a process for the stabilization of cholesterol ester hydrolase (cholesterol esterase; E.C. 3.1.1.13) from Pseudomonas in aqueous solution which optionally contains a surface-active agent.

Cholesterol esterases are used to a considerable extent in reagents for the enzymatic analysis of cholesterol ester-containing solutions and especially of serum in clinical diagnosis.

These enzymes bring about the liberation of cholesterol from its esters with long chained fatty acids, which is subsequently determined by appropriate detection processes, usually enzymatically with the use of reactions catalysed by cholesterol oxidase (E.C. 1.1.3.6).

For the determination of this esterified cholesterol in serum, cholesterol esterase from Pseudomonas is especially suitable since it also has a lipase activity. An enzyme with this property is described, for example, in Federal Republic of Germany patent specification No. 28 19 384. Such enzymes are able to remove the turbidities brought about by the triglyceride content of the sample material in the reaction batch (clarification) and thereby, for example, to exclude disturbances in the case of photometric measurement processes.

Such cholesterol esterases with lipase activity can also be used for the detection of triglycerides in the sample material if the liberated glycerol is subjected to an appropriate detection reaction.

Furthermore, enzymes of this kind find general use in reagents for serum analysis with which neither cholesterol esters nor triglycerides are to be determined but in which, for measurement-technical reasons, a removal of the turbidities brought about by the triglycerides from the sample material is desirable.

It is known that cholesterol esterases in a buffered medium which contains no other components manifest towards their substrates no or only a very-low hydrolytic activity. Therefore, it is necessary to add activators to the reaction mixture.

As activators, there can be used many surface-active substances (detergents), such as non-ionic detergents, for example alkyl or aryl or aralkyl alcohol polyglycol ethers (Triton X-100, thesit, Lutensol ON 60 and 70 and isotridecyl ethers), and/or anionic detergents, for example salts of bile acids or of their conjugates.

The activating action is frequently assisted by an increased ionic strength in the reaction medium, the optimum ionic strength thereby being produced most simply by an appropriate dosing of the buffer substances.

As buffers, there can be used those which are most effective in the region of the activity optimum of the cholesterol esterases, i.e. mostly at a pH value of from 5 to 9. Phosphate buffers are especially preferred, which is to be seen from the available literature on cholesterol esterases.

As cholesterol esterases, there are mostly used enzymes of animal or microbial origin. However, between the different enzymes, there can, in some cases, be considerable differences in the activity spectrum with regard to the range of cholesterol fatty acid esters occurring in the serum. Vahouny, Weersing and Treadwell (Arch. Biochem. Biophys., 107, 7-15/1964) have described a cholesterol esterase from pancreatic juice, the enzymatic activity of which remains substantially uninfluenced by the nature of the chain length of the fatty acid ester, whereas from Z. Klin. Chem. Klin. Biochem., 12, 403-407/1974, a microbial cholesterol esterase is known, the hydrolytic activity of which is relatively highly dependent upon the nature of the fatty acid moiety of the cholesterol esters.

Furthermore, cholesterol esterases are known which are not able to react triglycerides or are only able to react them at a low rate of reaction, such as is described, for example, in J. Biol. Chem., 237, 3469-3656/1962.

The above-mentioned cholesterol esterase from Pseudomonas displays, with regard to the nature of the fatty acid moiety of the cholesterol esters, a very broad activity spectrum, also simultaneously reacts triglycerides with a high velocity under appropriate reaction conditions and would, therefore, for the initially mentioned reasons, be quite especially suitable for the production of reagents for the analysis of cholesterol ester- and/or triglyceride-containing solutions, for example serum.

However, the use of the enzyme for this purpose requires it to be sufficiently stable in the reagent ready for use, i.e. in aqueous solution.

We have now found that the enzyme from Pseudomonas admittedly still possesses a sufficient stability in pure phosphate buffer which is conventionally employed for the production of commercially available reagents for the determination of serum total cholesterol but, surprisingly, rapidly loses its activity when the phosphate buffer solution contains a surface-active agent of the above-mentioned kind, for example Triton X-100 or isotridecyl ethers, as activator. Consequently, it cannot be readily used in reagent solutions of which, for reasons of practicability and cost, there is demanded a storage stability which corresponds at least to that of cholesterol esterases of other origin known from the prior art.

Therefore, it is an object of the present invention to overcome these considerable disadvantages and to provide a process with the help of which the cholesterol esterase is stabilised in such a manner that, in the reagents which are ready for use, it can be stored for comparatively long periods of time, i.e. at least 3 to 5 days at ambient temperature, without substantial loss of activity.

Thus, according to the present invention, there is provided a process for the stabilisation of aqueous solutions of cholesterol esterase from Pseudomonas, especially in the presence of a surface-active agent, wherein the enzyme is dissolved in a phosphate-free buffer which contains 10 to 200 mMol/liter of magnesium ions.

The concentration of the magnesium ions is preferably adjusted to from 25 to 150 mMol/liter and more preferably from 50 to 100 mMol/liter.

As buffers, there can be used substances such as tris/tris/HCl, triethanolamine/triethanolamine hydrochloride, imidazole, HEPES, MOPS and other phosphate-free buffer mixtures, tris buffer preferably being employed. The pH value of the buffer solution is from 5.0 to 9.0, preferably from 6.5 to 9.0 and especially preferably from 7.5 to 8.5, particularly when tris buffer is employed.

The unstabilising effect of phosphate in the case of the Pseudomonas enzyme, especially in the presence of surface-active agents, is surprising and was not to have been deduced from the available literature concerning cholesterol esterases.

Thus, in J. Biol. Chem., 228, 447–457/1957, there is described a cholesterol esterase from pig pancreas, the enzymatic activity of which in phosphate buffer is measured with taurocholate as enzyme activator. A disadvantageous influence of the phosphate buffer on the properties of the enzyme is not mentioned in this literature reference.

Furthermore, statements concerning the properties of cholesterol esterases are to be found in many literature references, for example in J. Biol. Chem., 75, 1073–1079/1974; Biochim. Biophys. Acta, 231, 194–197/1971; Arch. Biochem. Biophys., 100, 360–363/1963; Clin. Chem., 20, 470–475/1974; and Biochim. Biophys. Acta, 384, 138–145/1975. In all of these literature references, the determination of the enzyme activity takes place in phosphate buffer-containing solutions, some of which contain surface-active materials, no mention thereby being made either of an unstabilising action of the phosphate or of a stabilising action of magnesium salts on the cholesterol esterases.

The same applies to literature references which are concerned with microbial cholesterol esterases.

Finally, the use of a microbial cholesterol esterase in a reagent for the fully enzymatic determination of serum cholesterol is described in Z. Klin. Chem. Klin. Biochem., 12, 403–407/1974. In addition to the use of thesit as detergent, the reagent also contains a comparatively high concentration of ammonium phosphate buffer, attention thereby being drawn to the good stability of the esterase-containing reagent.

The properties of a cholesterol esterase from *Pseudomonas fluorescens* is to be found in Agric. Biol. Chem., 39, 1511–1512/1975. The activity of the enzyme is determined by methods similar to those described in Clin. Chem., 20, 470–475/1974, the reagent in this case also being buffered with phosphate.

Therefore, a destabilising action of phosphate ions on the cholesterol esterase from Pseudomonas in the presence of surface-active agents was not known so that there was no reason to keep phosphate ions out of aqueous solutions of such cholesterol esterases. It was also not foreseeable that this effect can be overcome by the addition of magnesium ions in the above-given concentration range.

The present invention is admittedly of especial importance for the stabilisation of cholesterol esterases from Pseudomonas in solutions which contain a surface-active agent but, according to the present invention, a better maintenance of the activity of this enzyme in aqueous solution can also be achieved when no surface-active agent is present.

Cholesterol esterase from Psueodmonas is known and commercially available. It has already been found in many different strains of Pseudomonas, for example in *Pseudomonas fluorescens* (see Federal Republic of Germany Patent Specification No. 28 19 384) and in Pseudomonas sp. (see Federal Republic of Germany Patent Specification No. 2 33 646). In the case of all investigated cholesterol esterase preparations from Pseudomonas, the process according to the present invention has proved to be very effective, regardless of which cholesterol esterase-containing strain of Pseudomonas has been used as the source of the enzyme. This follows from investigations which have been carried out with Pseudomonas sp. DSM 1280, commercially-available cholesterol esterase from *Pseudomonas fluorescens* (SIGMA, Cat. No. C 1770) and Pseudomonas sp. DSM 1281 cholesterol esterase. The cholesterol esterase from these three strains of Pseudomonas were each investigated in a solution which contains, as surface-active agent, 10 mMol sodium cholate and 0.3% polyethoxy-fatty alcohol ether.

The results obtained are shown in the accompanying drawings, in which:

FIG. 1 is a graphic representation in which the percentage activity during storage at 25° C. is plotted. The curve formed by the circles refers to the enzyme solution in potassium phosphate buffer 0.1 Mol/liter, pH 7.6; the curve formed by the triangles refers to the enzyme in tris.HCl buffer 0.1 Mol/liter, pH 7.0; and the curve formed by the black spots refers to tris.HCl 0.1 Mol/liter, pH 7.6, containing 50 mMol/liter magnesium aspartate;

FIG. 2 corresponds to FIG. 1 but for commercially-available esterase from *Pseudomonas fluorescens;* and FIG. 3 corresponds to FIG. 1 but for cholesterol esterase from Pseudomonas sp. DSM 1281.

The magnesium ions can be added in the form of any desired magnesium salt, the anion of which does not have a disadvantageous effect on any of the components of the enzyme solution. Besides the magnesium salts of inorganic acids, for example magnesium chloride or magnesium sulphate, there are especially preferred the magnesium salts of organic acids, such as fatty acids, dicarboxylic acids and amino acids. The magnesium salts of amino acids are preferred, especially magnesium aspartate.

The stabilising action of the magnesium ions on the cholesterol esterase from Pseudomonas is not an activating action. This is supported by the fact that in a solution containing a surface-active agent, there is no difference with regard to activity whether magnesium aspartate or sodium chloride is added in comparable concentration, the latter possessing no stabilising action. This is also supported by the fact that a cholesterol esterase from Pseudomonas substantially inactivated by storage in a detergent-containing phosphate buffer is not reactivated by the subsequent addition of magnesium salts, even in comparatively high concentrations, i.e. up to the solubility limit in phosphate buffer.

By means of the present invention, it is possible so to stabilise the cholesterol esterase from Pseudomonas in aqueous solution, which, on the basis of its properties, is especially preferred for the determination of esterified cholesterol, that the desired storage stability is achieved.

The improved stability achieved according to the present invention is further demonstrated by the following Examples, in which the following abbreviations are used:

CHE = cholesterol esterase from Pseudomonas
HEPES = N-2-hydroxyethylpiperazine-N′-ethanesulphonic acid
tris = tris-(hydroxymethyl)-aminomethane
isotridecyl ether = polyoxyethylene isotridecyl ether
thesit = polyoxyethylene dodecyl ether
MOPS = 3-(N-morpholino)-propanesulphonic acid
Triton×100 = polyoxyethylene isooctylphenyl ether
Lutensol ON 60 and ON 70 = polyoxyethylene fatty acid alcohol ether.

EXAMPLE 1

The stability of the CHE was investigated at 25° C. in various buffers with and without the addition of magnesium ions. The following Table 1 shows the results achieved with four different buffers and different surface-active agents, without the addition of magnesium ions, and Table 2 shows the corresponding results obtained in the case of adding 50 mM magnesium ions. In all cases, use was made of 10 mMol/liter of cholate and 0.3% of the stated non-ionic surface-active agent.

TABLE 1

| non-ionic surface-active agent | buffer 100 mM | CHE-stability (%) |   |   |   |   |   |
|---|---|---|---|---|---|---|---|
|   |   | 1d | 2d | 4d | 7d | 10d | 14d |
| isotridecyl ether | K—phosphate pH = 7.6 | 21 | 14 | 11 | 0 |   |   |
|   | tris pH = 7.6 | 77 | 61 | 39 | 16 | 5 | 0 |
|   | imidazole pH = 7.6 | 78 | 72 | 50 | 10 | 8 | 6 |
|   | MOPS pH = 7.0 | 87 | 74 | 43 | 46 | 33 | 27 |
| Triton X-100 | K—phosphate | 2 | 0 |   |   |   |   |
|   | tris | 58 | 34 | 0 |   |   |   |
|   | imidazole | 57 | 35 | 10 | 2 | 0 |   |
|   | MOPS | 76 | 53 | 20 | 9 | 7 | 0 |

TABLE 2

| non-ionic surface-active agent | buffer | CHE-stability (%) |   |   |   |   |   |
|---|---|---|---|---|---|---|---|
|   |   | 1d | 2d | 4d | 7d | 10d | 14d |
| isotridecyl ether | tris pH = 7.6 | 102 | 102 | 83 | 52 | 45 | 40 |
|   | imidazole pH = 7.6 | 84 | 87 | 71 | 55 | 43 | 38 |
|   | MOPS pH = 7.0 | 96 | 82 | 63 | 61 | 58 | 56 |
| Triton X-100 | tris | 85 | 77 | 50 | 36 | 35 | 30 |
|   | imidazole | 75 | 60 | 33 | 25 | 30 | 20 |
|   | MOPS | 92 | 82 | 53 | 51 | 45 | 34 |

The above results show that, in the case of the combination according to the present invention of phosphate-free buffer and magnesium ions, the stability is considerably improved.

EXAMPLE 2

The dependence of the stabilising action upon the magnesium concentration was investigated at 25° C. in 100 mM tris buffer, pH 7.6. The results obtained are shown in the following Table 3. With regard to the surface-active agents, there again apply the remarks made in Example 1.

TABLE 3

| non-ionic surface active agent | $Mg^{2+}$ conc. mM. | CHE-stability (%) |   |   |   |   |   |
|---|---|---|---|---|---|---|---|
|   |   | 1d | 2d | 4d | 7d | 10d | 14d |
| isotridecyl ether | 0 | 77 | 61 | 39 | 16 | 5 | 0 |
|   | 10 | 102 | 94 | 81 | 53 | 33 | 33 |
|   | 50 | 102 | 102 | 83 | 52 | 45 | 40 |
|   | 100 | 98 | 92 | 79 | 64 | 56 | 49 |
|   | 150 | 104 | 102 | 93 | 68 | 61 | 56 |
| Triton X-100 | 0 | 58 | 34 | 0 |   |   |   |
|   | 30 | 65 | 51 | 17 | 19 | 10 | 7 |
|   | 50 | 85 | 77 | 50 | 36 | 35 | 30 |
|   | 100 | 93 | 85 | 66 | 43 | 35 | 32 |
|   | 150 | 96 | 81 | 35 | 34 | 31 | 30 |

The results given in Table 3 show that even in the case of a magnesium ion concentration of 10 mM, the stability is considerably increased.

EXAMPLE 3

As described in Example 1, the stability of the CHE with and without the addition of magnesium ions was investigated in different buffers and with different surface-active agents. However, in contradistinction to Example 1, the solution was kept at 4° C. The following Table 4 shows the stability without magnesium and Table 5 the stability with

TABLE 4

| non-ionic surface-active agent | buffer | CHE-stability (%) |   |   |   |   |   |   |   |
|---|---|---|---|---|---|---|---|---|---|
|   |   | 2d | 3d | 7d | 14d | 21d | 28d | 35d | 42d |
| isotridecyl ether | K—phosphate pH = 7.6 | 35 | 13 | 2 | 0 |   |   |   |   |
|   | tris pH = 7.6 | 93 | 63 | 54 | 48 | 32 | 28 | 21 | 18 |
|   | imidazole pH = 7.6 | 85 | 60 | 57 | 50 | 37 | 28 | 28 | 22 |
|   | MOPS pH = 7.0 | 81 | 60 | 58 | 60 | 60 | 55 | 47 | 40 |
| Triton X-100 | K—phosphate | 29 | 13 | 13 | 8 | 0 |   |   |   |
|   | tris | 58 | 35 | 31 | 25 | 13 | 6 | 2 | 0 |
|   | imidazole | 65 | 43 | 35 | 35 | 35 | 30 | 24 | 20 |
|   | MOPS | 74 | 47 | 36 | 29 | 17 | 11 | 8 | 7 |

TABLE 5

| non-ionic surface-active agent | buffer | CHE-stability (%) |   |   |   |   |   |   |   |
|---|---|---|---|---|---|---|---|---|---|
|   |   | 2d | 4d | 7d | 14d | 21d | 28d | 35d | 42d |
| isotridecyl ether | tris pH = 7.6 | 110 | 77 | 75 | 75 | 67 | 67 | 55 | 58 |
|   | imidazole pH 7.6 | 89 | 62 | 78 | 60 | 53 | 55 | 47 | 47 |
|   | MOPS pH = 7.0 | 87 | 44 | 73 | 71 | 69 | 69 | 55 | 56 |
| Triton X-100 | tris | 67 | 45 | 63 | 49 | 55 | 55 | 45 | 38 |
|   | imidazole | 102 | 62 | 60 | 50 | 45 | 40 | 35 | 30 |
|   | MOPS | 79 | 55 | 43 | 45 | 32 | 26 | 17 | 18 |

A comparison of the values from Table 5 with the values from Table 2 shows that, according to the present invention, the stability at ambient temperature is just as good as at a cold storage temperature.

EXAMPLE 4

In the manner described in Example 2, there was investigated the dependence of the CHE stability on the magnesium ion concentration but at 4° C. All the other conditions correspond to those of Example 2. The results obtained are given in the following Table 6.

TABLE 6

| non-ionic surface-active agent | Mg²⁺ conc. (mM) | CHE-stability (%) | | | | | | | |
|---|---|---|---|---|---|---|---|---|---|
| | | 2d | 4d | 7d | 14d | 21d | 28d | 35d | 42d |
| isotri-decyl ether | 0 | 93 | 63 | 54 | 48 | 32 | 28 | 21 | 18 |
| | 10 | 110 | 74 | 69 | 71 | 61 | 61 | 46 | 46 |
| | 50 | 110 | 77 | 75 | 75 | 67 | 67 | 55 | 58 |
| | 100 | 92 | 66 | 72 | 68 | 56 | 70 | 62 | 59 |
| | 150 | 93 | 79 | 81 | 77 | 70 | 70 | 63 | 63 |
| Triton X-100 | 0 | 58 | 35 | 31 | 25 | 13 | 6 | 2 | 0 |
| | 10 | 71 | 44 | 47 | 34 | 30 | 22 | 22 | 17 |
| | 50 | 67 | 45 | 63 | 49 | 55 | 55 | 45 | 38 |
| | 100 | 97 | 58 | 48 | 26 | 25 | 24 | 26 | 24 |
| | 150 | 95 | 61 | 65 | 52 | 46 | 65 | 52 | 46 |

We claim:

1. Process for the stabilisation of an aqueous solution of cholesterol esterase from Pseudomonas, wherein the enzyme is dissolved in a phosphate-free buffer which contains 10 to 200 mMol/liter of magnesium ions.

2. Process according to claim 1, wherein 25 to 150 mMol/liter of magnesium ions are added.

3. Process according to claim 2, wherein 50 to 100 mMol/liter of magnesium ions are added.

4. Process according to claim 1 wherein the buffer used has a pH value of from 5.0 to 9.0.

5. Process according to claim 4, wherein the buffer used has a pH value of from 6.5 to 9.0.

6. Process according to claim 5, wherein the buffer used has a pH value of 7.5 to 8.5.

7. Process according to claim 1 wherein an anionic and/or non-ionic surface-active agent is present.

8. A stabilized aqueous solution of cholesterol esterase from Pseudomonas, comprising said cholesterol esterase dissolved in a phosphate-free buffer containing 10 to 200 mMol/liter of magnesium ions.

9. Process according to claim 2 wherein the buffer used has a pH value of from 5.0 to 9.0.

10. Solution according to claim 8 wherein the buffer used has a pH value of from 5.0 to 9.0.

* * * * *